United States Patent [19]

Smets et al.

[11] Patent Number: 5,182,378
[45] Date of Patent: Jan. 26, 1993

[54] SULFATE DERIVATIVES OF GALACTAN EXTRACTED FROM KLEBSIELLA

[75] Inventors: Pierre Smets, Villennes sur Seine; Rene Zalisz, Menucourt, both of France

[73] Assignee: Roussel Uclaf, Paris, France

[21] Appl. No.: 622,719

[22] Filed: Dec. 4, 1990

[30] Foreign Application Priority Data

Dec. 4, 1989 [FR] France .................. 89 15972

[51] Int. Cl.$^5$ .............. C08B 37/00; A61K 31/70; A61K 31/715
[52] U.S. Cl. ..................... 536/4.1; 536/122; 536/124
[58] Field of Search .......... 536/122, 124, 4.1; 514/54, 25, 8, 885

[56] References Cited

U.S. PATENT DOCUMENTS

| | | | |
|---|---|---|---|
| 3,856,943 | 12/1974 | Birkenmeyer | 536/16.3 |
| 3,892,729 | 7/1975 | Birkenmeyer | 536/16.5 |
| 4,751,218 | 6/1988 | Smets et al. | 536/4.1 |
| 4,840,941 | 6/1989 | Ueno et al. | 514/54 |
| 4,877,777 | 10/1989 | DiLuzio | 514/54 |
| 4,956,347 | 9/1990 | Ban et al. | 514/54 |
| 5,008,253 | 4/1991 | Casu et al. | 514/54 |
| 5,013,724 | 5/1991 | Petitou et al. | 514/54 |
| 5,017,565 | 5/1991 | Lange et al. | 514/54 |
| 5,032,401 | 7/1991 | Jamas et al. | 514/54 |

OTHER PUBLICATIONS

Sandström et al., "Anti-viral Theraphy in AIDS," AIDS Press Limited, pp. 373–390 (1987).
Mitsuya et al. "Retroviruses In Human Lymphoma/Leukemia," Protection of T Cells Against Infectivity and Cytopathic Effect of HTLV-III in Vitro, Japan Sci. Soc. Press, Tokyo/VMU Science Press, Utrecht.

*Primary Examiner*—Ronald W. Griffin
*Attorney, Agent, or Firm*—Bierman and Muserlian

[57] ABSTRACT

A sulfate derivative of galactan extracted from Klebsiella mainly comprised of sulfate neutral oses in a proportion of 20 to 90% of hydroxyls and their preparation and method of use.

9 Claims, No Drawings

SULFATE DERIVATIVES OF GALACTAN EXTRACTED FROM KLEBSIELLA

STATE OF THE ART

French Patent No. 2,574,429 describes acylglycan extracted from Klebsiella composed of approximately 80% neutral oses, 20% lipids, less than 2% proteins and having a molecular weight of approximately 12,500 and containing a chain formation of galactoses linked in position 1-3. They are endowed with antiallergic and immunomodulating properties. French Patent Application Ser. No,. 89.09305 filed on Jul. 11, 1989, and European Patent Applicaton No. 90-4019874 describe galactan of low molecular weight extracted from Klebsiella, its preparation process, its use as medicaments, notably immuno-stimulating medicaments.

OBJECTS OF THE INVENTION

It is an object of the invention to provide novel sulfate derivatives of galactan extracted from Klebsiella and a process for its preparation.

It is another object of the invention to provide novel HIV antiviral compositions and a method of treating HIV viral infections in warm-blooded animals.

These and other objects and advantages of the invention will become obvious from the following detailed description.

THE INVENTION

The novel sulfate derivatives of the invention of galactan extracted Klebsiella are comprised of sulfate neutral oses in a proportion of 20 to 90% of hydroxyls, preferably 50 to 70% of hydroxyls. The composition in neutral oses is determined by gas phase chromatography after methanolysis according to the method of ZANETTA, J. Chromato. (1972) Vol. 69, p. 291 or the method of KAMERLING (Biochem J. (1975) Vol. 101, p. 491).

The sulfate derivatives of galactan are characterized in that they are comprised of a linear chain formation of galactose in position 1-3 and have a molecular weight of 5,000 to 12,000, preferably close to 7,000. The polysaccharides are free from lipids and proteins.

The galactose composition is determined by gas phase chromatography, after reduction and methanolysis. The lipids are determined by gas phase chromatography after methanolysis and the proteins are determined by the method of LOWRY (J.B.C. (1951), Vol. 193, p. 265 to 273).

The sequence of the chain formation of the galactoses is determined by standard methods of methylation, analysis by gas phase chromatography coupled with mass spectrometry, periodic oxidation, NMR of $H^1$ and $C^{13}$. The results show that the galactan is formed of a linear chain formation of galactose residues connected by 50% of alpha (1-3) bonds and 50% of beta (1-3) bonds, with a repetition pattern composed of 8 galactopyranose residues and 1 galactofuranose residue.

The sulfate derivatives of galactan can be prepared from various species of Klebsiella. Quite particularly there is retained the sulfate derivative of galactan, characterized in that it comes from Klebsiella pneumoniae, and notably from the strain deposited at the Pasteur Institute in Paris or the Collection Nationale de Culture de Microorganismes (CNCM) under the numbers 52145 and I-163 and at the National Culture Type Collection under the No. 5055.

The process of the invention for the preparation of the new sulfate derivatives of galactan extracted from Klebsiella as defined above comprises treating an acylglycan extracted from Klebsiella mainly composed of approximately 80% neutral oses, 20% lipids, less than 2% proteins and having a molecular weight of approximately 12,500 by gentle acid hydrolysis, followed by high performance chromatography on an anion exchanger, recovering the unretained fraction, subjecting the said fraction to gel filtration, recovering the fraction containing the galactan of molecular weight of 4,000 to 10,000, sulfating the fraction of galactan thus obtained and purifying the latter by dialysis to obtain the sulfate derivative of galactan.

The acylglycan extracted from Klebsiella used at the beginning can be obtained from a water-soluble bacterial extract from Klebsiella by heating, followed by chromatographic fractionation. Such preparations have already been described in French Patent Application No. 2,574,429 and German Patent No. DE 3,543,267. The water-soluble bacterial extract from Klebsiella has been prepared according to processes described in French Patent No. 2,490,496 and European Patent No. 49,182.

In the preferred conditions for the process, the gentle acid hydrolysis of the acylglycan is carried out in a 1% solution of acetic acid by heating to 100° C. for 90 minutes. The precipitate formed which contains the lipid fraction is eliminated by centrifuging, for example for 30 minutes at 2,000 g. The supernatant which contains the galactan is collected and can be lyophilized. The galactan is then separated from the supernatant by chromatographic fractionation and the fraction composed of neutral oses is collected.

The fractionation can be carried out by chromatography on anion exchangers, preferably by high performance chromatography, for example on Magnum 9SAX Whatman. High performance chromatography on anion exchangers consists of separating the galactan by elution with water. The fraction composed of neutral oses is located by spectrophotometric detection at 200 nm and at 492 nm after coloration with the phenol-sulfuric acid test by the method of DUBOIS (Anal. Chem., (1956), Vol. 28, p. 350).

The said fraction constituted of neutral oses is subjected to gel filtration which allows the recovery of the fraction containing the galactan of molecular weight between 4,000 and 10,000. The gel filtration is carried out on commercially available supports, for example on Sehadex or Biogel agarose and Biogel A-1.5M is preferably used. The sulfation of the galactan fraction is carried out with a sulfonic acid such as chlorosulfonic acid in an amine such as pyridine or with a sulfonate such as piperidine N-sulfonate by heating the reaction medium. The dialysis is carried out against distilled water.

The HIV antiviral compositions of the invention are comprised of an HIV antivirally effective amount of a sulfate derivative of galactan extracted from Klebsiella comprised of sulfate neutral oses in a proportion of 20 to 90% of hydroxyls and an inert pharmaceutical carrier. The compositions may be in the form of tablets, dragees, capsules, granules, solutions, syrups, suppositories, lyophilized or not injectable preparations, pessaries, creams, ointments, lotions, drops, collyria and aerosols.

Examples of suitable excipients are talc, gum arabic, lactose, starch, magnesium stearate, cocoa butter, aqueous or non-aqeuous vehicles, fatty substances of animal or vegetable origin, paraffin derivatives, glycols, various wetting, dispersing or emulsifying agents and preservatives.

The compositions have remarkable immuno-stimulating properties as well as have a good tolerance. Notably it possesses the property of stimulating the production of $Il_1$ and TNF at the level of the macrophages and above all of stimulating the generation of free radicals (polynuclear). They also allow the synergy of the effect of the GM-CSF (Granulomonocyte-Colony Stimulating Factor) and a remarkable anti-elastase activity is noted, both against bovine pancreatic elastase, and against human leucocytary elastase. Also these compositions show an anti-coagulant activity.

These compositions are useful in the treatment or prevention in man of immuno-depression, infectious illnesses caused by bacteria or viruses, and especially by the AIDS virus, in the treatment of illness due to parasites, toxic infections, in the treatment of post- hospital and post-surgical infections and allergies of all origins. The compositions can also be used very advantageously in the treatment of bone marrow transplants and post-chemotherapy medullary aplasias.

The compositions are also useful in pneumology in the treatment of emphysema, pneumonia, bronchitis, pulmonary disorders caused by nicotinism or atmospheric pollution, in cardiology in the treatment of arthritis, as well as, for example, in dermatology in the treatment of psoriasis, burns, buloses and in the ageing of the skin, in gastro-enterology in the treatment of acute pancreatitis and in a general manner in the treatment of all affections implicating the malfunctioning of the elastase as well as in the treatment of thromboembolic illness.

The novel method of the invention for treating HIV viral infections in warm-blooded animals, including humans, comprises administering to warm-blooded animals an HIV antivirally effective amount of a sulfate derivative of galactan extracted from Klebsiella comprised of sulfate neutral oses in a proportion of 20 to 90% of hydroxyls. The compositions may be administered orally, rectally or parenterally and the usual daily dose is 0.0066 to 0.066 mg/kg depending on the condition treated, the specific composition and the method of administration.

In the following examples there are described several preferred embodiments to illustrate the invention. However, it should be understood that the invention is not intended to be limited to the specific embodiments.

EXAMPLE 1

Sulfate derivative of the qalactan extracted from Klebsiella 0.4 ml of chlorosulfonic acid were added to pyridine cooled to 0° C. in ice and after returning to ambient temperature, 25 mg of the galactan extracted from Klebsiella pneumoniae in suspension in 25 ml of pyridine was added. The mixture was heated for 3 hours at 80° C., then cooled to ambient temperature, diluted with 30 ml of distilled water and finally treated with 5 ml of 2.5 M solution of soda. The solution was concentrated under vacuum, dialyzed with distilled water for 3 days, frozen and lyophilized to obtain the desired sulfate derivative of galactan extracted from Klebsiella. In the product, the hydroxyls were sulfated in a proportion of 60% and the molecular weight was close to 7,000. Preparation of the galactan extracted from Klebsiella pneumoniae.

334 mg of acylglycans of Klebsiella (obtained as indicated in Example 1 of French Application No. 2,574,429 from the strain deposited at the Pasteur Institute under the No. I-163) were solubilized in 33.4 ml of a 1% acetic acid solution and the mixture was heated to 100° C. for 90 minutes. After cooling, the precipitate containing the lipid fraction was separated by centrifuging at 2,000 g for 30 minutes. The supernatant was lyophilized and 200 mg of residue were isolated which were dissolved in 4 ml of water. Chromatography took place using 1 ml of fractions on a high performance anion exchanger chromatography Whatman Magnum 9 SAX (9.4 mm×50 cm)column, eluting with water for 30 minutes at a flow rate of 2 ml minute with detection at 200 nm. The fraction containing the neutral oses, located at 492 nm, was isolated after the phenol-sulfuric test to obtain 55 mg of the neutral fraction by lyophilization.

Isolation of the galactan

The previous lyophilizate was dissolved in a water-acetic acid-pyridine (973-7-20) buffer and then it was subjected to filtration on gel by chromatography on a Biogel A.1.5M (2 cm×1.5m) column balanced with the same buffer. The fraction detected in the phenol-sulfuric test was collected and was sterilized by filtration on a 0.22 micron membrane and lyophilized to obtain 22 mg of the expected galactan.

EXAMPLE 2

Sulfate derivative of qalactan extracted from Klebsiella 4 ml of chlorosulfonic acid were added to pyridine cooled to 0° C. in ice and after returning to ambient temperature, 85 mg of the galactan extracted from Klebsiella pneumoniae (prepared as in the preparation of Example 1) in suspension in 24 ml of pyridine were added. The mixture was heated for 2 hours at 80° C., then cooled to ambient temperature and diluted with 30 ml of distilled water. The pH of the reaction mixture was brought to 6 by the addition of a 2.5M solution of sodium hydroxide and the solution was dialyzed with distilled water, then frozen and lyophilized to obtain 32 mg of sulfate derivative of galactan extracted from Klebsiella pneumoniae.

EXAMPLE 3

Tablets containing 1 mg of the product of Example 1 or 2 and sufficient excipient of lactose, starch, talc and magnesium stearate for a final weight of 100 mg were prepared.

EXAMPLE 4

Aerosols were prepared delivering doses each of which contained 0.5 mg of product of Example 1, 0.15 mg of emulsifying agent and 50.00 mg of propellant.

EXAMPLE 5

A cream contained 1 mg of the product of Example 2 and sufficient excipient of 2-octyl-dodecanol alcohol, ketostearylic alcohol, sodium sulfate, methyl and propyl parahydroxybenzoate and purified water for a final weight of 10 mg was prepared.

BIOCHEMICAL STUDY

The activity of the sulfate derivative of galactan extracted from Klebsiella was determined by measurement of the inhibition of syncitia [Gruters et al, Nature, Vol. 330, p. 74 to 77, (5 Nov. 1987)] and by determination of the protective activity exercised vis-a-vis certain cell cultures.

A) Preparation and titration of virus

1° / Preparation of virus

The supernatant of H 9 III$_B$ cells (chronically infected with HIV) were cultured for 48 hours starting with $10^5$ cells/ml and the centrifuged supernatant was filtered at 0.45 micron > aliquoted and stored at $-80°$ C.

2° / Titration of virus reverse transcriptase (RT)
On the fresh supernatant $4.0 \times 10^6$ cpm/cm$^3$
After thawing $4.5 \times 10^6$ cpm/cm$^3$
MT4 / MTT test
technique: 100 microliter dilutions of the virus in series in a microtitration plate
addition of 100 microliters of cellular suspension containing $5 \times 10^4$ MT4 cells
culture 7 days at 37° C., 5% $CO_2$
addition of MTT (tetrazolium salt viability coloring agent)
incubation 4 hours at 37° C.
halting the reaction by the addition of a hydrochloric acid solution in isopropane reading of the optical density (OD) at 540 nm (after dissolution of the crystals).

Results

The relationship of the optical density of the infected cells (viral cytotoxicity—weak OD) over the optical density of infected cells (viability and maximum OD) as a function of the dilution of the virus (average over 3 wells). The more the cells were infected, the more this relationship was weak.

B) Protective activity of the sulfate derivative of the galactan extracted from Klebsiella

1° / Inhibition of Syncitia

A co-culture of H 9 III cells (chronically infected $10^5$ cells/ml) with SUP T1 cells (non-infected: $2 \times 10^5$ cells/ml) was carried out and there was syncitia formation which was counted with a microscope. Each type of cell was pre-incubated or non-preincubated with the studied product for one night at 37° C. If there was no pre-incubation, the studied product was added to cells at the moment the culture was carried out. When there was inhibition of Syncitia formation in the treated cells relative to the control cells, the studied product was protective. The results obtained are shown hereafter.

TABLE 1

| Product Example 1 in micrograms/cm$^3$ | Percentage of inhibition | |
|---|---|---|
| | Test no. 1 | Test no. 2 | co-culture with the studied product without previous incubation

| Product Example 1 in micrograms/cm$^3$ | Test no. 1 | Test no. 2 |
|---|---|---|
| 1 | 0 | 10 |
| 10 | 42 | 17 |
| 100 | 100 | 100 |

TABLE 2 pre-incubation with the studied product for one night at 37° C. before the co-culture

| Product of Example 1 in micrograms/cm$^3$ | Percentage of inhibition | |
|---|---|---|
| | H 9 III cells | Sup Ti cells |
| 1 | 17 | 23 |
| 10 | 23 | 27 |
| 100 | 100 | 100 |

2° / MT4 / MTT Test

MT4 cells at $10^6$ cells/ml were used and dilution to ½ took place with or without the studied product at different concentrations. 100 microliters of HIV virus at different dilutions and 100 microliters of pre-treated cell suspension were introduced onto a microtitration plate. Incubation took place at 37° C. for 7 days and the MTT was added and a reading was taken with a spectrophotometer. The percentage inhibition of the infection of MT4 cells was determined and the results are shown hereafter:

TABLE 3

| Product of Example 1 in micrograms/cm$^3$ | Percentage of inhibition |
|---|---|
| 1 | 74 |
| 10 | 99 |
| 100 | 84 |

3° / H9 Test

H9 cells were used which were treated with polybrene, washed, and taken up in 100 microliters of medium, with or without the studied product at different concentrations. After incubating for 2 hours at 37° C. 100 microliters of HIV virus at 1/10 were added and the mixture was kept for 1 hour at 37° C. and then washed. The cells were taken up in 1 ml of medium with or without the studied product, and distributed into 2 wells, 500 microliters per well and $2 \times 10^5$ cells by well. On D+4, 500 microliters of culture medium with or without the studied product were added. On D+8, half of the supernatant was replaced with new medium. On D+11, a quantitative analysis by reverse transcriptase was carried out on the supernatant and an immunofluorescent determination was carried out on the cells. The results are shown hereafter.

TABLE 4

| | Reverse Transcriptase | | Immunofluorescence | |
|---|---|---|---|---|
| | cpm/cm$^3$ × $10^4$ | % inhibition | % fluorescent cells | % inhibition |
| Non-infected cells | 1.68 | | 0 | |
| Infected cells | 291 | | 51 | |
| Product of Example 1 (concentration in micrograms/cm$^3$ | | | | |
| 1 | 6.42 | 76 | 3 | 94 |
| 10 | 1.16 | 100 | 0 | 100 |
| 100 | 1.12 | 100 | 0 | 100 |

The results of the different tests show that the studied product very significantly inhibits the formation of syncitia and that it protects the studied cells from infection caused by the HIV virus.

Study of anti-elastase activity

The anti-elastase activity was determined by spectrophotometric quantitative analysis vis-a vis human leucocytary elastase by a similar technique to that described by Boulder et al., Clin. Chim. Acta., Vol. 132, p. 309 to 315 (1983).

| Product of Example | Human leucocytary elastase |
| --- | --- |
| 1 | Ki: $1 \times 10^{-8}$M |

Various modifications of the compositions and method of the invention may be made without departing from the spirit or scope thereof and it should be understood that the invention is intended to be limited only as defined in the appended claims.

What we claimed is:

1. A sulfate derivative of galactan extracted from Klebsiella mainly comprised of sulfate neutral oses in a proportion of 20 to 90% of hydroxyls with a linear chain formation of galactose in position 1-3 and having a molecular weight of 5,000 to 12,000 and free of lipids and proteins.

2. A sulfate derivative of galactan of claim 1 wherein the sulfate neutral oses are in a proportion of 40 to 80% of hydroxyls.

3. A sulfate derivative of galactan of claim 2 wherein the sulfate neutral oses are in a proportion of 50 to 70% of hydroxyls.

4. A sulfate derivative of galactan of claim 1 the extract comes from Klebsiella pneumoniae.

5. A sulfate derivative of galactan of claim 4 wherein the strain is deposited at the Pasteur Institute in Paris or the Collection Nationale de Culture de Microorganismes (CNCM) under numbers 52,145 and I-163 and at the National Culture Type Collection under the No. 5,055.

6. A process for the preparation of a derivative of claim 1 comprising subjecting an acylglycan extracted from Klebsillla comprising approximately 80% neutral oses, 20% of lipids, less than 2% of proteins with a molecular weight of about 12,500 to gentle acid hydrolysis and then to high performance chromatography on an anion exchanger, subjecting the non-retained fraction to gel filtration, sulfating the fraction containing galactan with a molecular weight of 4,000 to 10,000 and subjecting the sulfate derivative to dialysis.

7. The process of claim 6 wherein the sulfation was effected with a sulfonic acid in the presence of an amine and the dialysis is effected against distilled water.

8. The process of claim 7 wherein the sulfonic acid is chlorosulfonic acid and the amine is pyridine.

9. The process of claim 6 wherein the sulfation is effected with piperidine N-sulfonate with heating.

* * * * *